(12) United States Patent
Labreche et al.

(10) Patent No.: US 6,496,742 B1
(45) Date of Patent: Dec. 17, 2002

(54) CLASSIFYING APPARATUS DESIGNED IN PARTICULAR FOR ODOR RECOGNITION

(75) Inventors: Saïd Labreche, Toulouse (FR); Hicham Amine, Balma (FR); Tze Tsung Tan, Toulouse (FR); François Loubet, Balma (FR)

(73) Assignee: Alpha M.O.S., Toulouse (FR)

( * ) Notice: Subject to any disclaimer, the term of this patent is extended or adjusted under 35 U.S.C. 154(b) by 0 days.

(21) Appl. No.: 09/486,863
(22) PCT Filed: Sep. 4, 1998
(86) PCT No.: PCT/FR98/01896
§ 371 (c)(1),
(2), (4) Date: May 1, 2000
(87) PCT Pub. No.: WO99/12028
PCT Pub. Date: Mar. 11, 1999

(30) Foreign Application Priority Data

Sep. 4, 1997 (FR) ............................................. 97 11000

(51) Int. Cl.⁷ ................................................ G05B 13/02
(52) U.S. Cl. .............................. 700/47; 700/28; 700/30; 700/31; 700/46; 700/48; 700/50; 706/12; 706/15; 706/26; 706/45; 706/58; 382/155; 382/156; 382/181; 382/224; 382/228; 356/418; 356/419; 356/416; 702/22; 702/27; 702/28; 702/87; 436/43; 436/54; 436/55
(58) Field of Search .............................. 701/28, 29, 30, 701/31, 46, 47, 48, 49, 50; 706/2–6, 12, 14–16, 20–25, 31, 53, 45, 58; 382/155, 156, 159, 157, 228, 181, 224, 225, 227; 356/418, 416, 419; 702/22, 87, 28, 27; 436/43–55

(56) References Cited

U.S. PATENT DOCUMENTS 5,919,620 A * 7/1999 Brodeur et al. ................. 435/4

(List continued on next page.)

FOREIGN PATENT DOCUMENTS

| EP | 0527567 A2 | * 7/1992 | ........... G05B/15/02 |
| EP | 0 632 268 | 1/1995 | |

OTHER PUBLICATIONS

Ratton L et al., "A comparative study of signal processing techniques for clustering microssensor data (a first step towards an artificial nose)" Sensor and Actutors B. vol. 41, No. 1–3, Jun. 30, 1997, p. 105–120**, (List continued on next page.)

*Primary Examiner*—Ramesh Patel
(74) *Attorney, Agent, or Firm*—Weingarten, Schurgin, Gagnebin & Lebovici LLP

(57) ABSTRACT

A classification apparatus, notably for uses in recognition or characterisation of odors, comprises a plurality of sensors for generating raw data representing a plurality of instances of a plurality of different classes; and a processing unit for processing said raw data so as to determine an identification model. The identification model comprises definitions of the classes and a particular allocation rule selected dependent upon the application. The class definitions are established by analysing data obtained during a learning phase, the analysis being performed according to a particular information extraction method. During a later identification phase, the identification model enables an instance of unknown class to be allocated to an appropriate class amongst those defined during the learning phase. The information extraction method can be selected dependent upon the application. Preferably, a percentage of the data obtained during the learning phase is used to establish a plurality of candidate identification models, and the identification model which is selected for use is the one which gives the highest number of correct classifications when use to classify the other data obtained during the learning phase.

12 Claims, 4 Drawing Sheets

U.S. PATENT DOCUMENTS 5,946,640 A * 8/1999 Goodacre et al. ............ 700/266
6,192,351 B1 * 2/2001 Persaud ....................... 382/156
6,341,629 B1 * 1/2002 Clark et al. .................... 141/1

OTHER PUBLICATIONS

Horner G, "Signalverarbeitung Bei Chemosensorarrays" Technisches Messen TM. vol. 62, No. 4, Apr. 1, 1995, pp. 166–172**.

Wang Ping et al, "A Novel Method Combined Neural Network With Fuzzy Logic For Odour Recognition" Measurement Science and Technology, vol. 7, No. 12, Dec. 1996, pp. 1707–1217**.

Craven M A et al., "Electronic Noses–evelopment and Future Prospects" Trends in Analytical Chemistry, vol. 15, No. 9, Oct. 196, pp. 486–493**.

* cited by examiner

Search for specific regions

Discriminating Plane

Convex envelopes delimitating the different regions

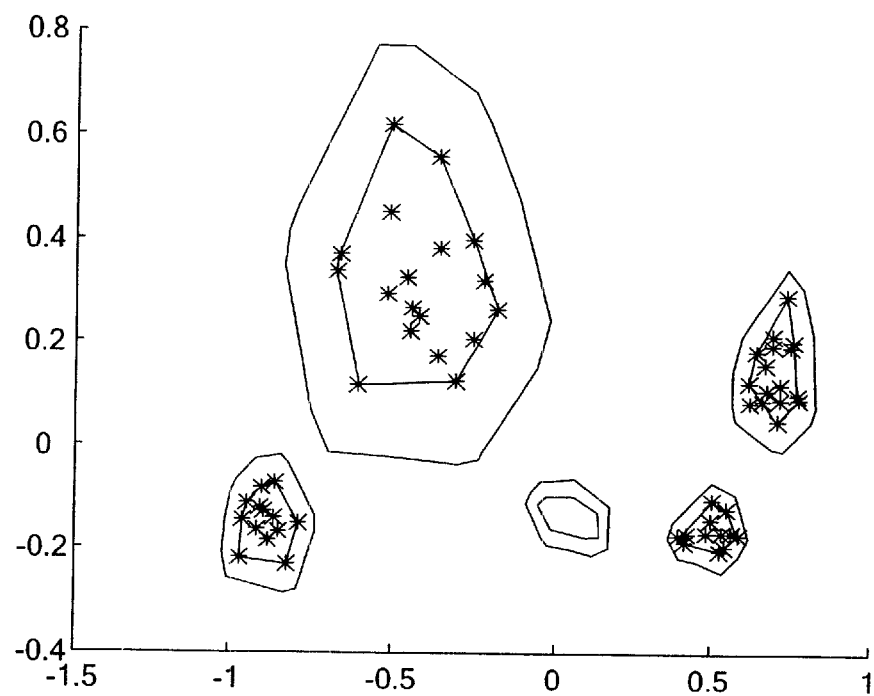
FIG. 4
Expansion of the different regions
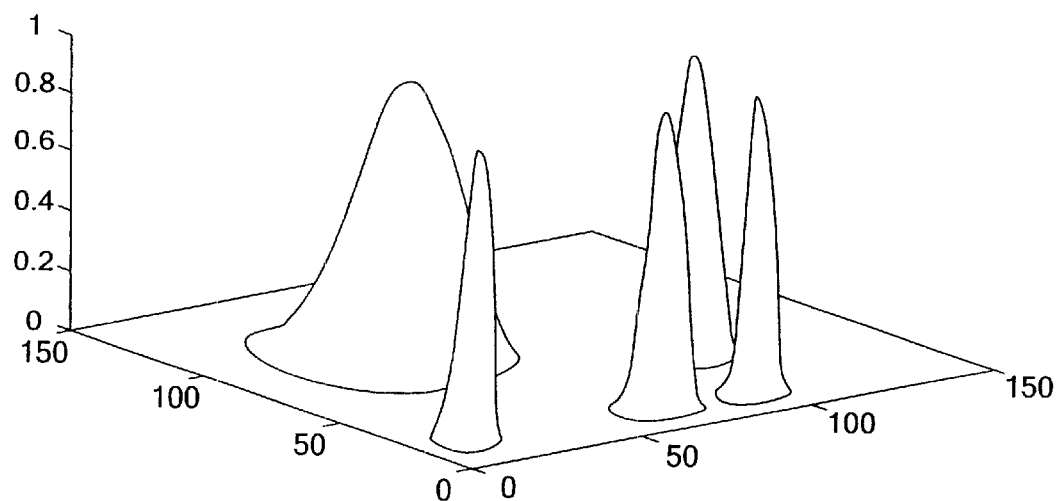
FIG. 5  Representation of the probability densities Choice of Model
Substitute

CLASSIFYING APPARATUS DESIGNED IN PARTICULAR FOR ODOR RECOGNITION

The present invention concerns pattern classification, notably in the field of the characterisation or the identification of odours and, more particularly, a pattern classification apparatus which selects, from a list, the appropriate classification rule dependent upon the application.

In odour characterisation or identification apparatus (so-called "electronic noses") a sample of an unknown product is identified by classifying it, according to a classification rule, in one of several classes which the apparatus recognises thanks to a preliminary learning operation during which the characteristics of the classes are determined.

Apparatus of this type comprises two main parts, a data acquisition portion and a data processing portion. In general, the data acquisition portion comprises a sampling head enabling the sampling of volatile components which are given off by the tested product, and a battery of sensors to which the sampled components are supplied and which produce output signals which, taken together, are characteristic of the volatile components given off by the product and, thus, are characteristic of the product. In general, the data processing portion comprises automatic data processing means which record the sensors' output signals and perform analyses thereon. By detecting or analysing the patterns inherent in the different sets of data relating to particular products, the data processing portion detects the class of the product, which can correspond either to the nature of the product (for example, "a wine", "a whisky", etc.), or to a concentration or quality of the product, for example, "fresh milk", "fermented milk", etc.

The goals pursued in acquiring and in processing the data are different depending upon whether the apparatus is in learning mode or in identification mode.

In the learning mode of the apparatus, the products from which the various samples are taken are known and are analysed several times. The processing methods which are used at this time are those which enable, on the one hand, the detection and characterisation of the different products and, on the other hand, the construction of a robust identification model. In general, an identification model consists of two elements, a method of extracting information from the sensors' output signals and an identification rule enabling data obtained for a sample of unknown nature to be classified into a particular class. The information-extraction methods used are, generally, statistical methods, notably a Principal Component Analysis (PCA) or Discriminant Factor Analysis (DFA) (see for example, J. W. Gardner and P. N. Bartlett, "Sensors and sensory systems for an Electronic Nose", Nato Asi, Series E, Vol. 212, pp.161–180 (1992)). In the identification phase, the nature of the samples is unknown and the goal is to identify this nature by using the data, and the model which has already been constructed.

Typically, apparatuses of this kind implement a fixed type of analysis of the data obtained during the learning phase so as to produce certain definitions of the classes and, during the identification phase, they apply a fixed rule to allocate the samples of unknown products into the appropriate one of the defined classes.

The present invention relates to a pattern classification apparatus, notably for use in the field of odour recognition, in which there is a choice between several different allocation rules and/or between several different information-extraction methods, so as to enable the identification model to be adapted to the intended application.

More particularly, the present invention provides a classification apparatus, notably for use in the recognition or the characterisation of odours, comprising: means for acquiring, by a plurality of channels, during a learning phase, raw data representing a plurality of instances of a plurality of different classes, it being known to which respective classes the instances analysed during the learning phase belong; a processing unit for processing the data provided by the data acquisition means so as to determine, during the learning phase, an identification model defining the different classes and, during an identification phase, to classify, using a particular rule, an instance of unknown class into one of the classes defined during the learning phase; characterised in that the processing means is adapted to decide which of a plurality of possible identification models, the characteristics of which are stored in a register, should be applied.

By choosing the allocation rule and/or the information-extraction method dynamically, dependent upon the intended application, the apparatus of the present invention reaches a rate of recognition of unknown products which is improved compared with the conventional apparatuses.

It is preferable to select in a dynamic fashion both the allocation rule and the method used for extracting the information from the measured raw data. Both of these elements form part of the identification model established during the learning phase of the apparatus. Preferably, the raw data processing unit uses, as information-extraction method, statistical processing such as a principal component analysis or a discriminant factor analysis. In general, these methods serve to determine respective sub-spaces in which the different classes are well-discriminated from each other.

Preferably, several different identification models are determined on the basis of only a percentage of the data obtained during the learning phase. The identification model which will be chosen is the one which gives the best recognition rate when the other data obtained during the learning phase is submitted thereto.

Among the different possible allocation rules there is a rule which defines the centre of gravity of the points representing the instances of a class and which allocates an unknown sample to the class for which the distance between the point representing the unknown instance and the centre of gravity is a minimum. There is also an allocation rule according to which the boundary delimiting the points representing the instances of one class from the points representing the instances of the other classes is determined, and an unknown instance is allocated to the class for which the expansion of the boundary needed in order to encompass the point corresponding to this unknown instance is a minimum. A third allocation rule consists in the establishment of a probability distribution, based on a weighted sum of Gaussian functions representing the instances of the different classes, and an instance of an unknown class is allocated to one of the classes based on the positioning of the point which represents it relative to this probability distribution.

In certain applications it can prove useful, or indeed necessary, to eliminate from the analyses the raw data relating to channels which do not contribute to differentiating the instances of different classes. It can also prove necessary to eliminate from the calculations the data relating to abnormal instances of a class, that is, instances which, in terms of synthetic variables, are far removed from the other instances of the same class. This increases the reliability of the identification model established during the learning phase. In the same way, the data obtained during the learning phase, relating to abnormal instances of a class, can be deleted.

Particular embodiments of the invention will now be described, as non-limiting examples, in association with the annexed drawings, in which:

FIG. 4 is a graph showing how the boundaries indicated in FIG. 3 can be expanded according to a variant of the identification rule in question;

FIG. 5 is a graph showing a probability distribution used by another identification rule according to the invention, corresponding to the five classes shown in FIG. 2.

Preferred embodiments of the apparatus according to the invention will now be described in the context of odour recognition apparatus. However, it is to be understood that the present invention is not limited to such applications but is equally well applicable in other fields where data representing instances of different classes must be classified.

A preferred embodiment of the invention will now be described with reference to FIGS. 1 to 6. This embodiment uses apparatus of the so-called "electronic nose" type, comprising p sensors. These sensors can include sensors of conventional types, such as, for example, conductive polymer sensors, quartz piezoelectric sensors; semiconductive oxide(s) sensors, etc. During the learning phase of the apparatus, several samples of known products are presented to the apparatus so as to generate raw data (a learning database) which will then be analysed to establish an identification model. This identification model is then used to classify samples of unknown products with respect to the classes established during the learning phase.

According to the preferred embodiment of the invention, several identification models are available. During the learning phase, the establishment of the identification model involves the selection of an information-extraction method enabling the characteristics of the different classes to be determined and the selection of an allocation rule which will be used, during the identification phase, to allocate unknown samples to one of the established classes. These choices are made dependent upon the intended application, that is, as a function of the characteristics of the products to be identified.

Before describing the method of selecting the extraction method and the allocation rule according to the invention, the preferred information-extraction methods and allocation rules will be presented.

INFORMATION EXTRACTION

Figure 1:
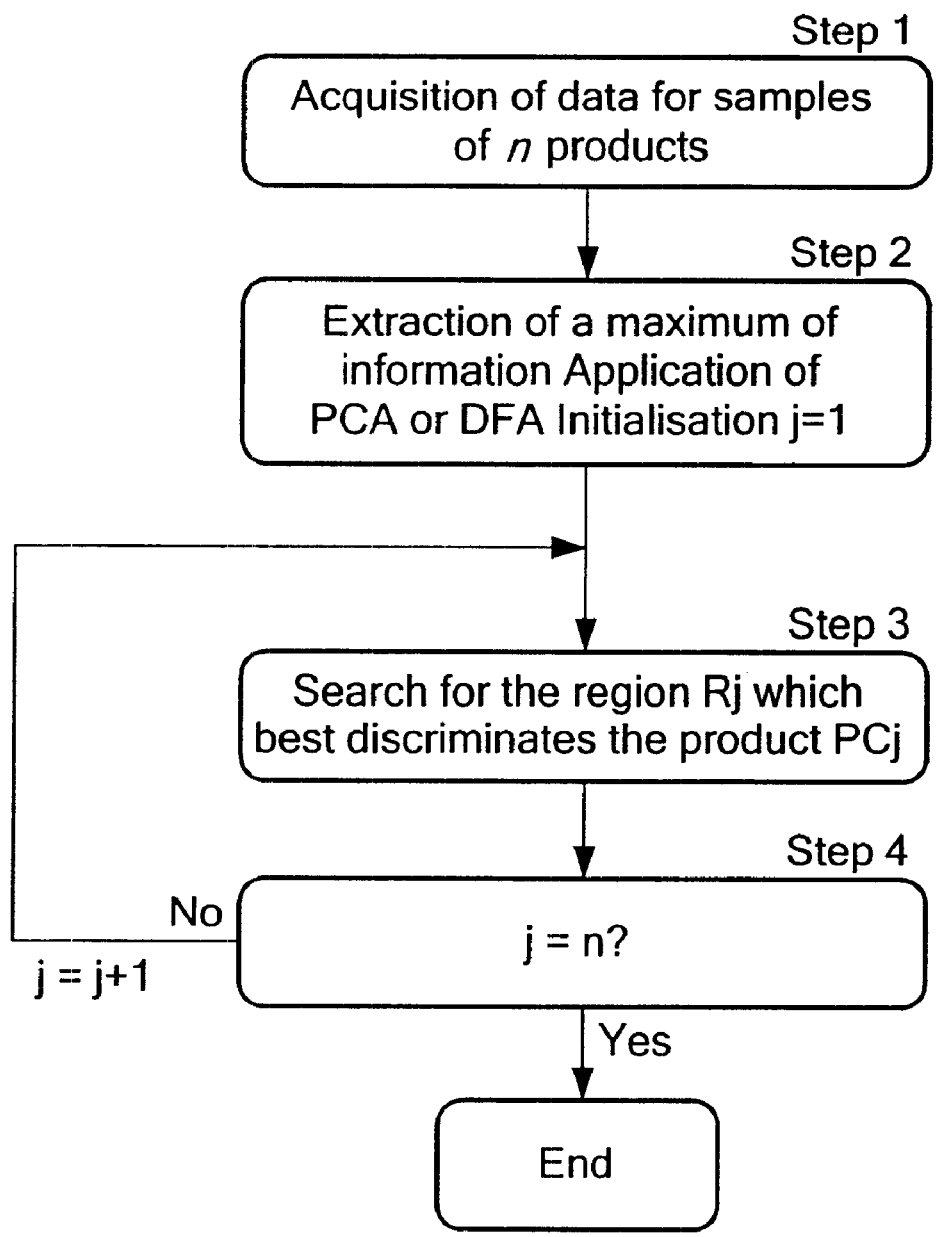
FIG. 1 is a flow diagram illustrating the different steps of the processing, for determining the characteristics of the different classes, which is applied in the preferred embodiment of the invention.

Several methods are possible for extracting information from the measured data. As indicated in FIG. 1, during the learning phase, data is acquired (Step 1) for samples of several known products. Next, this data is processed (Step 2) so as to extract information from it and to determine the characteristics common to the different instances of a class. The preferred information-extraction methods are Principal Component Analysis and Discriminant Factor Analysis, which enable the different instances (samples) to be represented as respective points in a sub-space of reduced dimensions. In general, the points representing instances of a common class form a cluster of points in the sub-space in question. There can thus be defined (Step 3) in the sub-space a respective region corresponding to each class such that the regions are distinct from one another. In other words, the definition of the regions ensures that the classes are well-discriminated from each other. Finally, a verification is made that discrimination regions have been defined for each class of product used in the learning phase (Step 4).

The different steps of this procedure will now be described in greater detail.

Establishment of a Learning Database

Several selected sensors are used in an "electronic nose". To each analysed sample i, there is associated a point $x_i$ in a p-dimensional space, p being the number of sensors.

$$x_i = \sum_{k=1}^{p} x(i,k) e_k$$

where k=1 to p
$e_k$ is a p-dimensional vector whose components are all equal to 0 except for the $k^{th}$ which is equal to 1. The set of these vectors forms a basis of the space. Here, $X(i,k)$ is the measurement given by the $k^{th}$ sensor during analysis of i. The set of these representations forms a "cloud" or distribution of points.

Generally, during the learning phase of this apparatus, several samples are analysed. Depending upon the applications, these samples can be derived from different products (PCJ/j=1 to n) or from the same product in different states (good, bad, borderline) or at different concentrations. At the end of the first stage of the learning phase (the "data acquisition" phase), there is, thus, obtained a data table or matrix X of dimensions (m,p), m being the total number of analysed samples (that is i takes the values 1 to m).

Processing of the Data

The goal now aimed at is to determine if the apparatus enables different products to be differentiated, the samples of a same product to be identified.

A metric M is defined over the space containing the points. Certain statistical items are also defined over the centred table X, in particular, the covariance matrices V, the interclass B and intraclass W variances, and the centres of gravity $(g_j/j=\{1;n\}$, n being the number of analysed products) of the classes defined by the samples of the different products (see, for example, G. Saporta "Probabilités, Analyse des données et Statistique", Editions TECHNIP (1990), for the calculation of these items).

Choice of Sensors

During the statistical pre-processing, the sensors which best discriminate the different products are chosen automatically. This choice is based on a step-by-step search for the best combination. M. C. Constanza and A. A. Afifi have proposed an appropriate alogorithm (in the Journal of the American Statistical Association, Vol.74, Number 368 (1979)). The non-selected sensors will not be taken into account in any of the analyses.

Determination of the Characteristics Common to the Instances of a Class

As has already been mentioned above, to each sample there is associated a point $\chi_i$ in a p-dimensional space and, in general, the points representing the instances of a single class are grouped and the different groups of points representing the different classes are separated from each other. The positioning of each group of points in the sub-space thus corresponds, in a way, to a definition of the class. Now, defining classes in a p-dimensional sub-space requires complex processing and the use of complicated mathematical expressions. Methods exist which enable the extraction, from the original data, of information enabling the discrimination of the classes one from the other in sub-paces of reduced dimensions. The preferred methods consist in a Principal Component Analysis or a Discriminant Factor Analysis. In each of these methods, a new basis is sought which optimises a well-defined mathematical criterion (see, for example, G. Saporta quoted supra). The application of these methods enables each sample to be associated with a vector possessing a reduced number of components.

PCA enables the selected sensors to be replaced by new synthetic variables (Cj, j={1;p}) which best discriminate the different products. In PCA, a particular basis (cj, j={1;p}) of the space is sought. The synthetic variable Cj is then associated with the vector cj.

The vectors (cj, j={1;p}) are the orthonormal eigenvectors M of the matrix VM. See, for example, Gene H. Golub & Charles F. Van Loan "Matrix Computations", The Johns Hopkins University Press (1990) for the calculation of the eigenelements. The synthetic variables are then defined by:

$$Cj(x)=x'M\ cj$$

where j={1;p}, x' being the transpose of x. Generally, M is associated with the identity matrix.

For its part, DFA enables the selected sensors to be replaced by new synthetic variables (Uj, j={1;p}) which best discriminate the different products. In DFA, a particular basis (uj, j={1;p}) of the space is sought. The synthetic variable Uj is then associated with the vector uj.

The vectors (uj, j={1;p}) are the orthonormal eigenvectors $W^{-1}$ of the matrix $BW^{-1}$. See supra Gene H. Golub & Charles Van Loan "Matrix Computations" for the calculation of the eigenelements. The synthetic variables are then defined by:

$$Uj(x)=x'W^{-1}uj$$

where j={1;p}, x' is the transpose of x and $W^{-1}$ is the inverse of the matrix W.

The exploration of the different sub-spaces generated by the new synthetic variables V (whether they are determined by PCA, DFA or by another method) enables the sub-space SEj to be found in which a class (here, a product) is best discriminated with regard to the others. This exploration or searching can be performed manually by visualising the different planes, or in an automatic fashion by searching for the best combination of these variables.

Figure 2:
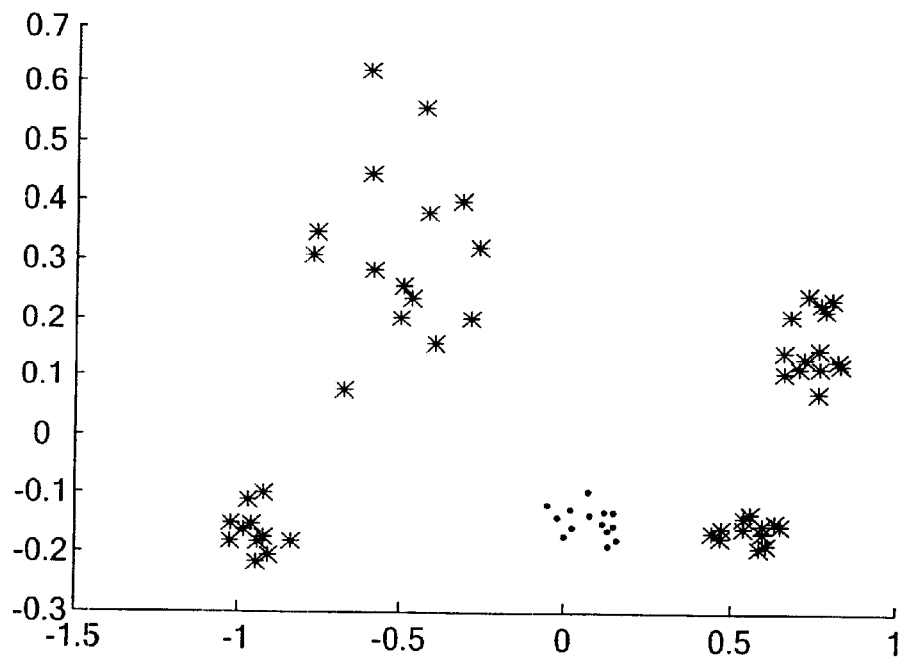
FIG. 2 is a graph showing the distribution of data obtained by a principal component analysis and representing instances of five different classes in a plane which enables the different classes to be differentiated from each other.

FIG. 2 illustrates an example of the results of a typical analysis and represents the projection of the samples of five products onto a plane defined by two synthetic variables obtained by a PCA. It will be seen that the different products are all well differentiated in this plane. In this case, all of the sub-spaces SEj are constituted by this single plane. In this case, it can be considered that each class corresponds to a region Rj of this common sub-space, the regions RI being defined in such a way as to ensure that each class is discriminated from the others.

Further, the statistical processing methods mentioned above also enable the detection of abnormal points the presence of which would distort the definition of the corresponding class. A sample of a product PCj will be identified as abnormal if, by eliminating this point, the variation in the volume or the surface area of the region Rj is greater than a certain percentage (for example, 10%). It is preferable that the detected abnormal points should be eliminated from the database. The elimination thereof enables the database to be filtered. The employed statistical method is then reapplied to the filtered database.

ALLOCATION RULES

It is not sufficient to determine the regions and/or sub-spaces corresponding to the different classes, it is also necessary to establish a rule enabling an unknown sample to be classified in or allocated to one of these classes since, a priori, the data representing this unknown sample might well correspond to a point located between two classes. Instead of choosing a fixed allocation rule, the present invention provides for the existence of a plurality of different rules, the choice of the appropriate rule being made during the learning phase of the apparatus. The preferred allocation rules according to the invention will now be described.

An unknown sample i can be associated with a point x(i,j) of the sub-space containing the specific region for the product PCj. Because this region is described in a particular sub-space SEj, x(i,j) is the projection onto this sub-space of the vector of recorded measurements. According to the present invention, there are three preferred rules for allocating this point to a particular class recognised by the apparatus. These three allocation rules consist, respectively, in (1) a rule based on a geometric criterion, (2) a rule based on a fuzzy criterion related to the boundary delimiting each class, and (3) a rule based on a probabilistic criterion.

1. Geometric Criterion (criterion (1)): Distance from the Centre

The set of points representing samples extracted from the same product is represented in a region associated with the latter. The product is represented by the centre of gravity $g_j$ of its points. The representation of the product PCj in the region associated with the latter is designated $g_j$.

$$g_j = \sum_i \frac{xi}{mj}$$

i is a sample of the product $PC_j$ and $m_j$ is the number of samples of this product.

Next, an unknown sample is identified with the product to which it is closest. That is, an unknown sample i is identified with the product $PC_k$ if:

$$dis(x(i,k),g_k)=\min(dis(x(i,j),g_j)/j=1{:}n)$$

dis(x(i,j),gj) is the distance between x(i,j) and $g_j$.

2. Fuzzy Criterion (criterion(2)): Boundary of the Region

Each region $R_j$ specific to a product is delimited by a boundary. This boundary is described by the convex envelope of the points representing the learning phase samples. One of the algorithms proposed in the literature is that given by B. Chazelle in ("Discrete Computational Geometry", 10, pp.377–409 (1993)). It enables such envelopes to be calculated in a multidimensional space.

Figure 3:
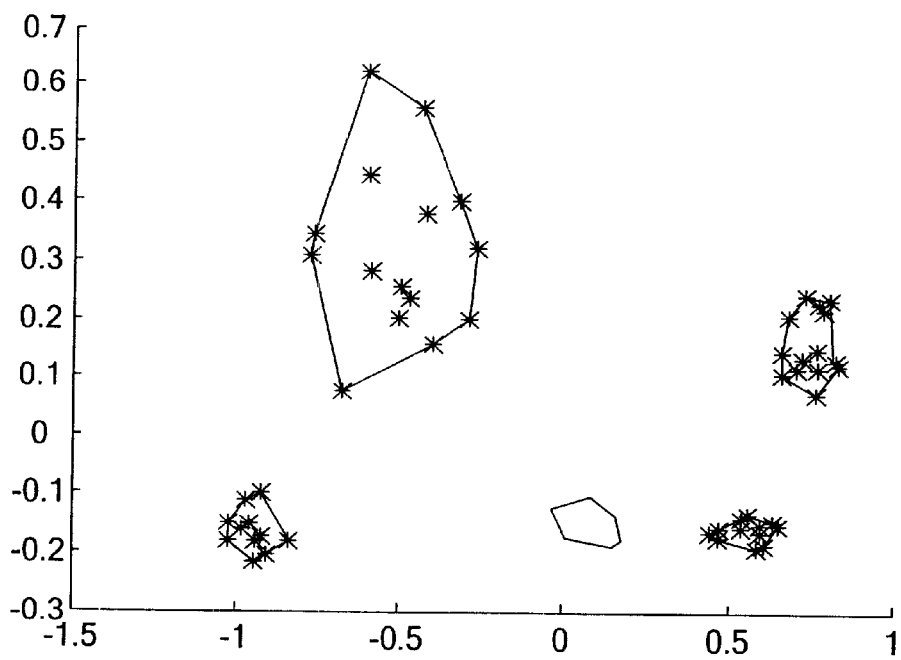
FIG. 3 is a graph showing the boundaries defined, according to a particular class identification rule, to delimit the regions corresponding to the different classes illustrated in FIG. 2.

In FIG. 3 there are shown the boundaries between the different regions represented in FIG. 2.

An unknown sample will be identified to a certain extent or degree with a product depending upon its position relative to this boundary. More particularly, a sample i will be classified in a class k if the amount of expansion of the volume/of the boundary of the region $R_k$ needed to encompass the point representing the sample i is the minimum of all the regions $R_j$. The volume or the surface area of the region delimited by this boundary is designated $V_j$ and the variation thereof is designated $\Delta(x(i,j),V_j)$, considering $x(i,j)$ as an element of $PC_j$. The "degree of belonging" is to defined by:

$$Deg(x(i, j), Vj) = 100 \times \left\{1 - \frac{\Delta(x(i, j), Vj)}{Vj + \Delta(x(i, j), Vj)}\right\}$$

An unknown sample is thus identified with the product PCk if $$Deg(x(i,k),Vk)=\max(Deg(x(i,j),Vj)/j=1:n)$$

From the definition of the convex envelope, it can be deduced that if $X(i,k)$ is within the boundary then the variation $\Delta(x(i,j),Vj)$ is zero. Consequently, the "degree of belonging" varies between 0 and 100.

So as to take into account small measurement variations, each region can be expanded as indicated in FIG. 4. The coefficient of expansion is a function of the volume or of the surface area of this surface.

3. Probabilistic Criterion (criterion (3)): Probability Density

Each region is associated with a probablility density function having a normal law Fj. This function is obtained by seeking the probability density function F of the cloud of points. Because the cloud is heterogeneous, this function is modelled by a weighted sum of n Gaussian functions. Thus, this gives:

$$F(x)=\Sigma\alpha j\ Fj(x) \text{ with } j=\{1;n\} \text{ and } \Sigma\alpha j=1$$

Fj being a Gaussian function, it is defined by a mean vector uj and a covariance matrix Wj. It is expressed by the formula:

$$Fj(x) = \frac{\exp(-(x-uj)'Wj^{-1}(x-uj)/2)}{\sqrt[p]{2\pi}\sqrt{det(Wj)}}$$

The different parameters $(\alpha j, uj, Wj)$ are estimated using an EM (estimation maximising) type algorithm (see R. A. Redner and H. F. Walker, SIAM review, 26, pp.195–239 (1984)).

An unknown sample is thus identified with the product $PC_k$ if $$Fk(x(i,k))=\max(\alpha j\ Fj(x(i,j))/j=1:n)$$

In FIG. 5 there are represented the values taken by the different densities in the regions Rj of FIG. 3, as well as the surroundings thereof. By normalising the different probability density functions, this third classification rule can be considered to be a fuzzy classification rule.

Suitability of the Criteria

The classification or allocation rule is chosen dependent upon the applications and the shapes of the regions associated with the different products.

1. The distance criterion is well suited to spherical-shaped structures. This is the case when the variations in the measurements recorded by the different sensors are of the same order.

2. The fuzzy criterion can be used in any case where the volume of the region associated with each product is different from zero. The expansion of the boundary enables small variations in the measurements to be taken into account.

3. Because the probability density function must be approximated, the number of samples of each analysed product must be large. The normalisation of each of these functions, that is, the transformation of each of these functions into a function varying between 0 and 1 enables a fuzzy classification rule to be defined.

Choice of the Model

An identification model is constituted by an information-extraction method (notably, PCA or DFA) and an identification criterion. It is designated Model(method,criterion). Depending upon the applications and the shapes of the structures of the different regions, one criterion is more or less suitable than another. A procedure for making a choice is, thus, necessary.

The preferred procedure for making this choice consists, first of all, in splitting the database into two databases Bc and Bi, the first database will be used for seeking the specific regions corresponding to the different classes and the second database will be used for the choice of the criterion. Because the products from which the different samples are extracted are known, for the samples in both databases, the criterion that will be chosen is the one that enables a maximum of the samples Bi to be identified.

The separation of the samples into the databases Bi and Bc does not follow any special rule. However, graphical representations of the measured points can be displayed so as to enable the user to select for the database Bc the points which are closest together (that is, the points which are well-grouped into the different classes). Taking into account the fact that the databases must be split and that the appropriate identification model is chosen based on analyses which are made on the databases Bi and Bc, it is necessary to have, in each database, data relating to classes having numbers of samples that are, on the one hand, significant and, on the other hand, balanced.

With PCA being designated method (1) and DFA being designated method (2), the chosen model (model(method(l) criterion(k))) is such that:

$$P(\text{method}(l)\text{criterion}(k))=\max(P(\text{method}(i)\text{criterion}(j))),$$

where i=1;2 and j=1;3.

Figure 6:
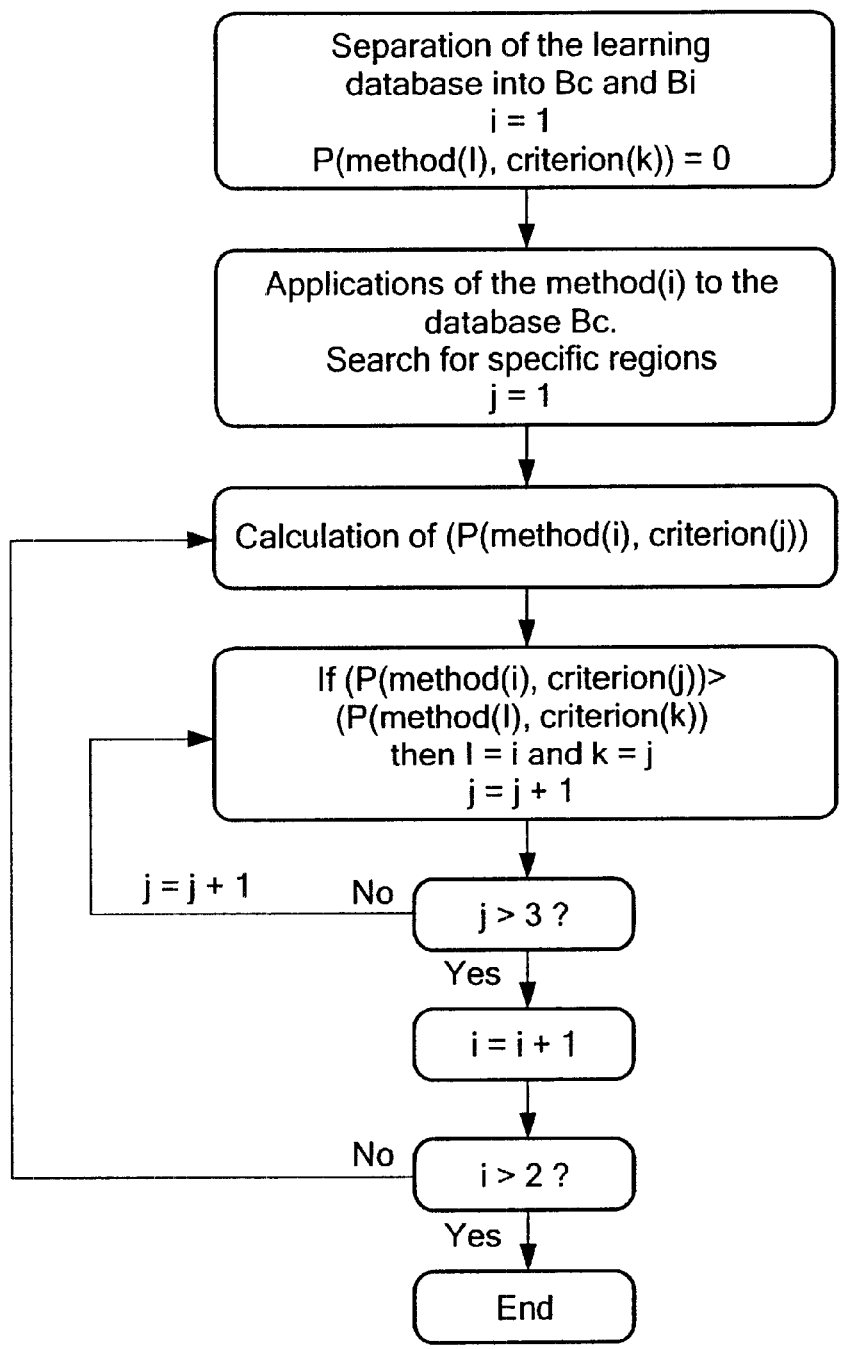
FIG. 6 is a flow diagram illustrating the different steps in a identification model selection procedure according to the preferred embodiment of the invention.

P(method(i)criterion(j)) is the percentage of samples of database Bi that are correctly classified using the criterion j in the regions defined by method i. The flow diagram of FIG. 6 summarises this procedure.

Although preferred embodiments of the invention have been described hereabove, it should be recalled that the present invention is not limited to these embodiments, which are described as non-limiting examples.

For example, the identification model can be modified during the identification phase. The sensor output signals relating to a sample identified as a member of a particular class with a sufficiently high degree of certainty can be introduced into the database established during the learning phase. The analysis is then performed afresh, taking this sample into account. This model can be very useful because it evolves and it takes into account small variations in the measurements due to parameters which are difficult to monitor or due to the ageing of the sensors.

What is claimed is:

1. Classification apparatus, comprising:

data acquisition means operable, in a learning phase, to acquire raw data by a plurality of channels, said raw data representing a plurality of instances of a plurality of different classes, wherein each instance analyzed during the learning phase belongs to a known class;

a processing unit for processing data provided by the data acquisition means, the processing unit being operable, in a learning phase, to determine an identification model comprising definitions of the different classes, and the processing unit being operable, during an identification phase, to classify an instance of unknown class into one of the classes defined during the learning phase, said classifying being performed according to a particular rule; and means for accessing a directory storing characteristics of a plurality of different identification models, each identification model comprising at least an allocation rule or an information-extraction method;

wherein the processing unit is operable, in the learning phase, to determine an identification model by selecting identification model characteristics stored in said directory.

2. Classification apparatus according to claim 1, wherein the processing unit is operable, in the learning phase, to select an allocation rule by choosing one rule from among a plurality of different possible rules stored in a list, the selected allocation rule forming part of the identification model determined by the processing unit during the learning phase.

3. Classification apparatus according to claim 2, wherein:

the processing unit is operable to calculate, for each instance, a vector x representing said instance, the different components of said vector x corresponding to data acquired in different channels for said instance by the data acquisition means; and one of the allocation rules of the list consists in a rule identifying, for each class (j), the volume or the surface area (Vj) of the boundary of the region (Rj) grouping together the instances of this class in a sub-space (SEj) in which this class is well-discriminated with respect to the others, said rule allocating an instance i of unknown class to a particular class (k) when:

$$\mathrm{Deg}(x(i,k),Vk)=\max(\mathrm{Deg}(x(i,j),Vj)/j=1;n)$$

where Deg(x(i,j),Vj) is the "degree of belonging" of the instance i to the class j calculated according to the following formula:

$$Deg(x(i,j),Vj) = 100 \times \left\{ 1 - \frac{\Delta(x(i,j),Vj)}{Vj + \Delta(x(i,j),Vj)} \right\}$$

and $\Delta(x(i,j),Vj)$ is the variation of the volume or of the surface area of the region Rj when the projection (x(i,j)) of the vector ($x_i$) representing the instance (i) of unknown class is considered as being a member of the class (j).

4. Classification apparatus according to claim 2, wherein:

the processing unit is operable to calculate, for each instance, a vector x representing said instance, the different components of said vector x corresponding to data acquired in different channels for said instance by the data acquisition means; and one of the allocation rules of the list consists in a rule classifying an instance (i) of unknown class into a particular class (k) when:

$$Fk(x(i,k))=\max(Fj(x(i,j))/j=1:n)$$

where Fj(x(i,j)) is a probability density function calculated for the class j based on the following formula:

$$Fj(x) = \frac{\exp(-(x-uj)' Wj^{-1} (x-uj)/2)}{\sqrt[P]{2\pi} \sqrt{\det(Wj)}}$$

5. Classification apparatus according to claim 1, wherein the processing unit is operable, in the learning phase, to select a method of extracting information from the raw data by choosing from a list one method from among a plurality of different possible methods stored in a list, the selected extraction method forming part of the identification model determined by the processing unit during the learning phase.

6. Classification apparatus according to claim 1, wherein the processing unit is operable, in the learning phase, to establish several candidate identification models based on data concerning only a percentage of the instances processed during the learning phase and to select from amongst these candidate identification models the model which gives the best percentage of correct classifications when the data representing the other instances processed during the learning phase is submitted thereto.

7. Classification apparatus according to claim 1, wherein:

the processing unit is operable to calculate, for each instance, a vector x representing said instance, the different components of said vector x corresponding to data acquired in different channels for said instance by the data acquisition means; and one of the allocation rules applicable by the processing unit consists in a rule identifying the closest class k to the vector $x_i$ representing an instance of unknown class according to the following formula:

$$\mathrm{dis}(x(i,k),g_k)=\min\ (\mathrm{dis}(x(i,j),g_j)/j=1;n)$$

where x(i,j) is the projection of the vector $x_i$ onto a sub-space SEj in which the class j is well-discriminated with respect to the other classes, dis(x(i,j),gj) is the distance between x(i,j) and $g_j$, and $g_j$ is a point representing the class j and calculated according to the formula:

$$g_i = \sum_l \frac{xl}{mj}$$

where 1 is an instance of the class j, and mj is the number of instances of this class used to establish the definition of the class.

8. Classification apparatus according to claim 1, wherein one of the information extraction methods consists of a principal component analysis.

9. Classification apparatus according to claim 1, wherein one of the information extraction methods consists of a discriminant factor analysis.

10. Classification apparatus according to claim 1, wherein the processing unit is operable to identify channels which do not help in differentiating between instances of different classes, and to determine the identification model based on data excluding the data from the channel or channels thus identified.

11. Classification apparatus according to claim 1, wherein the processing unit is operable to identify abnormal instances of a class and to determine the identification model based on data excluding the data relating to the thus-identified abnormal instances, the processing unit being operable to identify an instance as abnormal when a point defined by co-ordinates corresponding to data of different channels acquired by the data acquisition means for said instance is greater than a threshold distance away from the points corresponding to the other instances of the class.

12. Odor recognition apparatus, comprising:

data acquisition means operable, in a learning phase, to acquire raw data by a plurality of channels, said raw data being derived from odors and representing a plurality of instances of a plurality of different classes, wherein each instance analyzed during the learning phase belongs to a known class;

a processing unit for processing data provided by the data acquisition means, the processing unit being operable, in a learning phase, to determine an identification model comprising definitions of the different classes, and the processing means being operable, during an identification phase, to classify an instance of unknown class into one of the classes defined during the learning phase, said classifying being performed according to a particular rule; and means for accessing a directory storing characteristics of a plurality of different identification models, each identification model comprising at least an allocation rule or an information-extraction method;

wherein the processing unit is operable, in the learning phase, to determine an identification model by selecting identification model characteristics stored in said directory.

* * * * *

UNITED STATES PATENT AND TRADEMARK OFFICE
CERTIFICATE OF CORRECTION

PATENT NO. : 6,496,742 B1  Page 1 of 1
DATED : December 17, 2002
INVENTOR(S) : Saïd Labreche et al.

It is certified that error appears in the above-identified patent and that said Letters Patent is hereby corrected as shown below:

<u>Column 5,</u>
Line 60, "RI" should read -- $R_j$ --; and

<u>Column 11,</u>
Line 14, "means" should read -- unit --.

Signed and Sealed this

Twenty-seventh Day of April, 2004

JON W. DUDAS
*Acting Director of the United States Patent and Trademark Office*